United States Patent
Li et al.

(10) Patent No.: US 10,520,441 B2
(45) Date of Patent: Dec. 31, 2019

(54) DEVICES TO DETECT A SUBSTANCE AND METHODS OF PRODUCING SUCH A DEVICE

(71) Applicant: Hewlett-Packard Development Company, L.P., Houston, TX (US)

(72) Inventors: Zhiyong Li, Foster City, CA (US); Ning Ge, Palo Alto, CA (US); Steven J. Barcelo, Palo Alto, CA (US); Huei Pei Kuo, Cupertino, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 342 days.

(21) Appl. No.: 14/775,839

(22) PCT Filed: Mar. 14, 2013

(86) PCT No.: PCT/US2013/031613
§ 371 (c)(1),
(2) Date: Sep. 14, 2015

(87) PCT Pub. No.: WO2014/142913
PCT Pub. Date: Sep. 18, 2014

(65) Prior Publication Data
US 2016/0025635 A1    Jan. 28, 2016

(51) Int. Cl.
*B82Y 30/00* (2011.01)
*G01N 21/65* (2006.01)
(Continued)

(52) U.S. Cl.
CPC ............. *G01N 21/658* (2013.01); *C25D 1/02* (2013.01); *C25D 1/20* (2013.01); *G01N 21/648* (2013.01);
(Continued)

(58) Field of Classification Search
CPC .... G01N 21/658; G01N 21/648; G01N 27/04; G01N 27/22; C25D 1/02; C25D 1/20; B82Y 15/00; B82Y 35/00; B82Y 30/00
(Continued)

(56) References Cited

U.S. PATENT DOCUMENTS 6,368,871 B1 *   4/2002   Christel ............... B01F 5/0403
                                                      204/450
6,874,861 B2 *   4/2005   Farr ..................... B41J 2/17566
                                                      347/19
(Continued)

FOREIGN PATENT DOCUMENTS

CN       1957245       5/2007
JP       H06-240488    8/1994
(Continued)

OTHER PUBLICATIONS

International Search Report and Written Opinion, Korean IPO, dated Jan. 16, 2014. Hewlett-Packard Development Company, L.P., PCT Application No. PCT/US2013/031613.
(Continued)

*Primary Examiner* — Brian R Gordon
(74) *Attorney, Agent, or Firm* — Hanley Flight & Zimmerman LLC (57) ABSTRACT

Devices to detect a substance and methods of producing such a device are disclosed. An example device to detect a substance includes a housing defining a first chamber and a substrate coupled to the housing. The substrate includes nanostructures positioned within the first chamber. The nanostructures are to react to the substance when exposed thereto. The device includes a first heater positioned within the first chamber. The heater is to heat at least a portion of the substance to ready the device for analysis.

20 Claims, 6 Drawing Sheets

(51) Int. Cl.
*B82Y 35/00* (2011.01)
*C25D 1/02* (2006.01)
*C25D 1/20* (2006.01)
*G01N 21/64* (2006.01)
*G01N 27/04* (2006.01)
*G01N 27/22* (2006.01)
*G01N 33/02* (2006.01)
*G01N 33/22* (2006.01)

(52) U.S. Cl.
CPC ............ *G01N 27/04* (2013.01); *G01N 27/22* (2013.01); *B82Y 30/00* (2013.01); *G01N 33/02* (2013.01); *G01N 33/22* (2013.01); *G01N 2201/068* (2013.01)

(58) Field of Classification Search
USPC ......... 422/404, 502–503, 551–552, 554, 414
See application file for complete search history.

(56) References Cited

U.S. PATENT DOCUMENTS

| | | | | |
|---|---|---|---|---|
| 7,342,656 | B2* | 3/2008 | Islam | G01N 21/658 356/301 |
| 7,866,201 | B1* | 1/2011 | Tutu | G01N 7/00 73/19.05 |
| 8,593,629 | B2* | 11/2013 | Santori | B82Y 20/00 356/301 |
| 2002/0118027 | A1* | 8/2002 | Routkevitch | A61L 27/06 324/694 |
| 2006/0038990 | A1* | 2/2006 | Habib | G01N 21/658 356/301 |
| 2007/0132043 | A1* | 6/2007 | Bradley | B82Y 10/00 257/414 |
| 2007/0140900 | A1 | 6/2007 | Wang et al. | |
| 2007/0177139 | A1* | 8/2007 | Kamins | G01N 21/658 356/301 |
| 2007/0254377 | A1* | 11/2007 | Li | G01N 21/658 436/171 |
| 2008/0128274 | A1 | 6/2008 | Raghurama et al. | |
| 2008/0187648 | A1* | 8/2008 | Hart | B01J 23/745 427/8 |
| 2008/0199861 | A1* | 8/2008 | Gu | B01L 7/52 435/6.11 |
| 2008/0219895 | A1* | 9/2008 | Sasaki | G01N 33/005 422/83 |
| 2009/0207413 | A1 | 8/2009 | Carpenter et al. | |
| 2009/0318307 | A1* | 12/2009 | Garcia Tello | C12Q 1/6827 506/12 |
| 2010/0050751 | A1* | 3/2010 | Lee | G01N 35/00029 73/64.56 |
| 2011/0053794 | A1* | 3/2011 | Zhang | B01J 19/0046 506/9 |
| 2011/0163636 | A1* | 7/2011 | Sirbuly | B82Y 30/00 310/339 |
| 2011/0252512 | A1 | 10/2011 | Kim | |
| 2011/0294154 | A1 | 12/2011 | Jaron et al. | |
| 2012/0081703 | A1* | 4/2012 | Moskovits | G01N 21/658 356/301 |
| 2012/0149021 | A1* | 6/2012 | Yung | B03C 1/01 435/6.12 |
| 2012/0164745 | A1* | 6/2012 | Fu | G01N 21/658 436/164 |
| 2012/0212732 | A1* | 8/2012 | Santori | B82Y 20/00 356/301 |
| 2012/0236304 | A1* | 9/2012 | Lee | G01N 21/658 356/301 |
| 2012/0267041 | A1* | 10/2012 | Woo | B32B 37/02 156/230 |
| 2013/0040862 | A1* | 2/2013 | Li | G01N 21/658 506/20 |
| 2013/0196449 | A1* | 8/2013 | Kim | G01N 21/658 436/501 |
| 2014/0065034 | A1* | 3/2014 | Zheng | G01N 30/6095 422/502 |
| 2014/0186215 | A1 | 7/2014 | Shinta et al. | |
| 2014/0209463 | A1* | 7/2014 | Gibson | B03C 5/005 204/547 |
| 2015/0177151 | A1* | 6/2015 | Hu | G01N 21/658 356/301 |
| 2016/0003732 | A1* | 1/2016 | Li | G01N 21/648 356/301 |
| 2016/0003770 | A1* | 1/2016 | Klootwijk | G01N 27/4146 73/31.06 |
| 2018/0143136 | A1* | 5/2018 | Barcelo | G01N 21/645 |

FOREIGN PATENT DOCUMENTS

| | | |
|---|---|---|
| JP | 2005-076068 | 3/2005 |
| WO | WO-2012172971 | 5/2012 |

OTHER PUBLICATIONS

Lv, Wenlong, et al. "Design and simulation of electrostatic inkjet head." Nano/Micro Engineered and Molecular Systems (NEMS), 2010 5th IEEE International Conference on. IEEE, 2010.
"Preparation, Characterization and Surface-enhanced Raman Scattering Activity of Silver Nanoparticles" Jia HuiYing.

* cited by examiner

FIG. 14

DEVICES TO DETECT A SUBSTANCE AND METHODS OF PRODUCING SUCH A DEVICE

CROSS-REFERENCE TO RELATED APPLICATION

This application is a U.S. National Stage Application of and claims priority to International Patent Application No. PCT/US2013/031613, filed on Mar. 14, 2013, and entitled "DEVICES TO DETECT A SUBSTANCE AND METHODS OF PRODUCING SUCH A DEVICE," which is hereby incorporated by reference in its entirety.

BACKGROUND

Surface Enhanced Raman Spectroscopy (SERS) may be used in various industries to detect the presence of an analyte. For example, SERS may be used in the security industry to detect and/or scan for explosives (e.g., detecting and/or scanning baggage at airports for explosives and/or other hazardous materials). Alternatively, SERS may be used in the food industry to detect toxins or contaminates in water and/or milk.

Certain examples are shown in the above-identified figures and described in detail below. The figures are not necessarily to scale and certain features and certain views of the figures may be shown exaggerated in scale or in schematic for clarity and/or conciseness.

DETAILED DESCRIPTION

Many applications have a need for a reliable device that can be employed to detect the presence of a substance of interest. For example, such testing or detecting devices are useful to detect the presence of explosives, toxins or hazardous substances at airports, manufacturing facilities, food processing facilities, drug preparation plants, etc. The substrates of some known testing and/or detecting devices are not sufficiently protected against premature exposure to the environment and/or a substance (e.g., an analyte) that the substrate is intended to detect. Prematurely exposing the substrate to the environment and/or the substance (e.g., an analyte) may cause the substrate to oxidize and/or to not be as effective in detecting the substance once intentionally exposed thereto.

Example testing and/or detecting devices for the analysis of various substances are disclosed herein. In some such examples, the testing device is for use with surface Enhanced Raman spectroscopy, Enhanced Fluorescence spectroscopy or Enhanced Luminescence spectroscopy, which may be used to detect the presence of the substance of interest in or on the testing or detecting device. Example testing devices disclosed herein include metal and/or conductive orifice plates and/or housings that protect a substrate of the testing device from exposure to the environment and/or reduce (e.g. prevent) oxidation or other contamination of the substrate and/or associated surface structures prior to use. Additionally, in contrast to some known devices, testing devices disclosed herein include one or more ink slot(s), one or more a sensor(s) and/or one or more heater(s). The ink slot(s) may be used to controllably and/or precisely deliver a solution or chemical to a testing chamber of the testing device. The one or more sensor(s) may be implemented by a sensing capacitor that measures impedance and/or capacitance of the solution or chemical to identify a parameter and/or property thereof. The one or more heater(s) may be implemented by a low temperature resistance heater used to quickly dry the solution or chemical to ready the testing device for further analysis.

In some examples, the testing device includes an orifice plate, a substrate on which nanostructures/nanoparticles are positioned, a sensor and a heater. In some examples, to couple and/or integrate the orifice plate with the wafer and/or substrate, a concave side of the orifice plate is positioned to face the substrate such that a chamber is defined between the orifice plate and the wafer and/or substrate. In some such examples, the sensor, the heater, the nanostructure(s) and/or the nanoparticles are positioned within the chamber. Positioning the nanostructure(s) and/or the nanoparticles within the chamber substantially prevents the nanostructure(s) and/or nanoparticles from being prematurely exposed to a substance that the nanostructure(s) and/or nanoparticles are intended to detect. The orifice plate may be coupled to the wafer and/or substrate using a gang-bond process (e.g., thermocompression bonding to bond metals). To reduce or even prevent the unintentional exposure of the nanostructure(s) and/or nanoparticles to a substance such as an analyte that the nanostructure(s) and/or nanoparticles are intended to detect, a polymer tape covers a fluidic inlet port(s), an aperture(s), etc., of the orifice plate.

To use the example testing and/or detecting devices to attempt to detect a substance of interest, in some examples, the polymer tape is at least partially removed from the orifice plate to expose one or more fluidic port(s), one or more aperture(s), the chamber, the substrate, the nanostructures and/or the nanoparticles to the environment, chemical, substance, gas, analyte, etc., to be tested. Additionally or alternatively, to use the testing device to attempt to detect a substance of interest, a substance or chemical may be controllably delivered to the chamber through an aperture and/or slot defined by the testing device and/or substrate. After the substrate, nanostructure and/or nanoparticles have been exposed to the environment and/or substance (e.g., chemical, gas, analyte, etc.) whose presence is to be detected and/or tested for, the sensor may measure a value of a parameter (e.g., impedance) of the substance. To determine a characteristic of the substance based on the measured parameter, a processor may compare the measured parameter to one or more reference parameters. Additionally or alternatively, after the substrate, nanostructure and/or nanoparticles have been exposed to the environment and/or substance (e.g., chemical, gas, analyte, etc.), the heater may heat the substance to increase the rate at which the substance dries on the nanostructure(s) and/or nanoparticles to more quickly ready the testing device, nanostructures and/or nanoparticles for further analysis.

After exposure to the environment and/or substance, and/or after the substance dries on the nanostructure(s) and/or nanoparticles, the testing device is placed in or adjacent to an example reading device. The reading device may include a light source that illuminates the substrate, nanostructure and/or nanoparticles. In some examples, the light scattered by the substrate, nanostructure and/or nanoparticles (e.g., Raman scattering in Surface Enhanced Raman spectroscopy, fluorescence in Enhanced Fluorescence spectroscopy or luminescence in Enhanced Luminescence spectroscopy) is monitored using a spectrometer, photodetector, etc., having appropriate guiding and/or filtering components. In some examples, the results obtained by the reading device are displayed on a monitor and/or are indicative of detection or no detection of the substance being tested and/or looked for.

Figure 1:
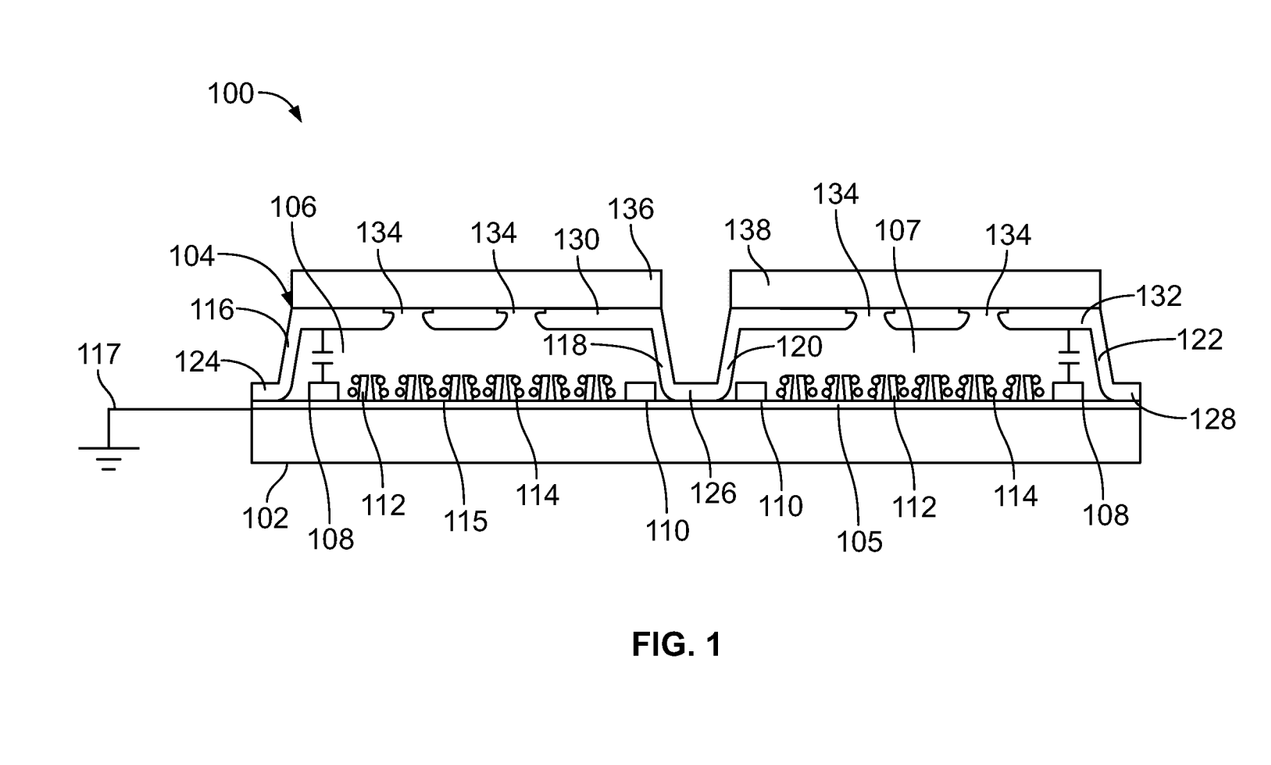
FIG. 1 depicts an example testing device constructed in accordance with the teachings of this disclosure.

FIG. 1 depicts an example testing and/or detection device 100 constructed in accordance with the teachings of this disclosure. The testing device 100 of the illustrated example includes a substrate 102 coupled to a metallic and/or conductive orifice plate and/or housing 104 via a bondpad 105. In the illustrated example, the orifice plate 104 defines first and second chambers 106, 107 in which a sensor 108, a heater 110, nanostructures 112 and/or nanoparticles 114 are positioned. The nanostructures 112 and/or nanoparticles 114 may be conical and/or pillar shaped. In some examples, after exposure to a substance or chemical, the pillar structures are pulled together to form nanoparticle assemblies having controllable geometries for enhanced spectroscopy analysis. In some examples, after exposure to a substance or chemical, the conical structures have relatively sharp tips that produce relatively strong enhancement for spectroscopy analysis. In some examples, the substrate 102 is transparent to enable detection and/or analysis of the nanostructures 108 and/or nanoparticles 110 through the substrate 102.

The sensor 108, the heater 110, the nanostructures 112 and/or the nanoparticles 114 of the illustrated example are positioned adjacent and/or coupled to a surface 115 of the substrate 102 and/or the bondpad 105. The substrate 102 of the illustrated example may be made of any suitable material such as glass, plastic, paper, Polydimethylsilsoxane, a transparent material, rubber and/or a membrane, for example. The orifice plate 104 of the illustrated example may be made of any suitable material such as metal, nickel, gold and/or platinum, for example. The nanoparticles 114 of the illustrated example may include gold and/or silver and/or any other element or chemical that may react with, respond to, collect, etc., a substance of interest such as an analyte.

The nanostructures 112 and/or the nanoparticles 114 of the illustrated example facilitate detection of an analyte to which they have been exposed. In some examples, the analyte is contained in a solution or chemical added to the chamber 106, 107. The sensor 108 of the illustrated example is grounded 117. The example sensor 108 of this example is implemented by a sensing capacitor that measures impedance and/or capacitance of the solution or chemical added to the chamber 106, 107. The measured values from the sensor 108 are used to determine a characteristic of the solution or chemical. The heater 110 of the illustrated example is implemented by a low temperature resistance heater (e.g., a resistor) used to quickly dry the solution or chemical to ready the testing device 100 for further analysis.

To define portions of the chambers 106, 107, the orifice plate 104 of the illustrated example includes tapered portions 116, 118, 120, 122, coupling portions 124, 126, 128 and top portions 130, 132 defining apertures and/or fluidic inlet bores 134. In some examples, the coupling portions 124, 126, 128 and the top portions 130, 132 are spaced apart and substantially parallel to one another and are coupled via the respective tapered portions 116, 118, 120, 122. As used herein, the phrase "substantially parallel" means within about a 10 degree skew of parallel. In other examples, the coupling portions 124, 126, 128 are spaced apart from the top portions 130, 132 but the coupling portions 124, 126, 128 are not parallel to the top portions 130, 132.

As illustrated in the example of FIG. 1, the first chamber 106 is defined by the tapered portions 116, 118 and the top portion 130. The second chamber 107 is defined by the portions 120, 122 and the top portion 132. In this example, the coupling portion 126 is coupled to the substrate 102. The coupling portion 122 and the substrate 102 are joined to form a hermetic seal to separate the first and second chambers 106, 107 such that a first substance may be added to the first chamber 106 and a second substance may be added to the second chamber 107 without intermingling.

To enclose the first and second chambers 106, 107 of the illustrated example, seals 136, 138 are removably coupled to the top portions 126, 128. The seals 136, 138 of the illustrated example are hermetic seals. The hermetic seals 136, 138 of the illustrated example may be made of polymer tape, plastic, a transparent material, plastic sheeting, foil material, foil sheeting, a membrane, wax and/or Polydimethylsiloxane.

Figure 2:
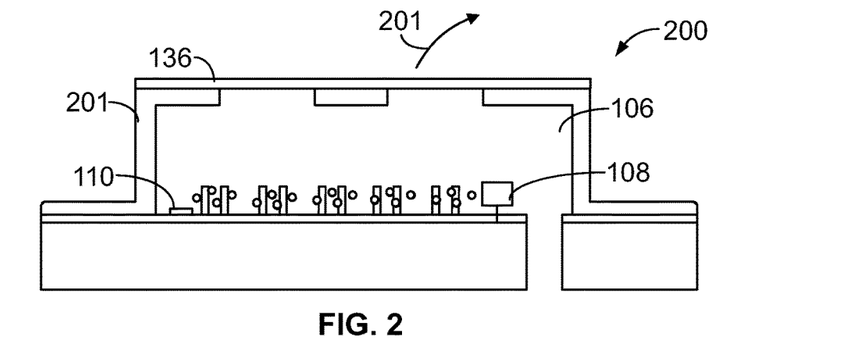
FIG. 2 depicts another example testing device with a seal coupled to an example orifice plate in accordance with the teachings of this disclosure.

FIG. 2 depicts an example testing and/or detecting device 200 with the seal 136 about to be removed in a direction generally indicated by arrow 201. The example testing device 200 of the example shown in FIG. 2 is similar to a first half of the testing device 100 of FIG. 1. As a result, detailed description of the same or similar parts for FIG. 1 will not be repeated herein. Instead, the interested reader is referred to the above description of the similar parts to facilitate the process. Like reference numerals are used to refer to like parts in FIGS. 1 and 2.

After the seal 136 is removed from an orifice plate and/or housing 201 of the testing device 200, air and/or other gas within a test environment (e.g., a room) in which the example testing device 200 is positioned flows through the apertures 134 and into the chamber 106 where it is exposed to the nanostructures 112 and/or nanoparticles 114. The air and/or other gas within the test environment may or may not include the analyte that the nanostructures 112 and/or the nanoparticles 114 are intended to detect.

Figure 3:
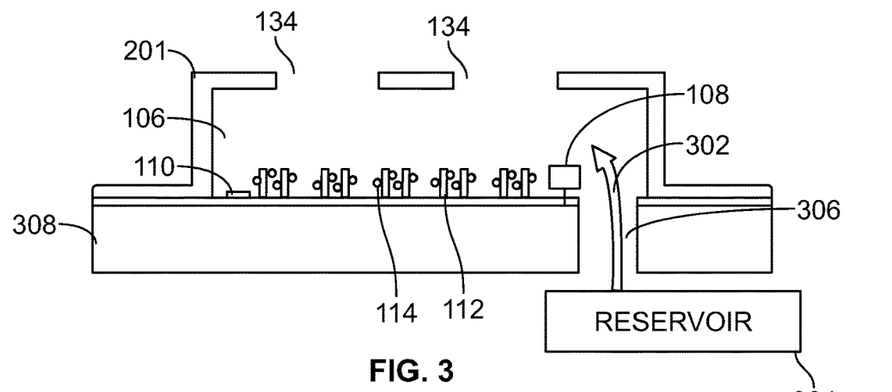
FIG. 3 depicts the example testing device of FIG. 2 with an analytic solution being added to the chamber.

FIG. 3 depicts the example testing and/or detecting device 200 after the seal 136 has been removed from the orifice plate 201. In the example of FIG. 3, a solution or chemical 302 to be analyzed is being added to the chamber 106 from a reservoir 304 through an aperture and/or slot 306 defined by a substrate 308. While FIG. 3 depicts the testing device 200 having the solution or chemical 302 added to the chamber 106 with the seal 136 removed, in other examples, the seal 136 may remain attached to the orifice plate 201 while the solution or chemical 302 is added to the chamber 106. Depending on the test circumstances, the solution or chemical 302 may or may not include the analyte that the nanostructures 112 and/or the nanoparticles 114 are intended to detect. In some examples, after the nanostructures 112 and/or the nanoparticles 114 have been exposed to the solution or chemical 302, the chamber 106 is re-covered by the seal 136 and/or another seal to ensure that the nanostructures 112 and/or nanoparticles 114 are not contaminated with exposure to a non-testing environment after the test has occurred. In some examples, after the nanostructures 112 and/or the nanoparticles 114 have been exposed to the solution or chemical 302, the sensor 108 measures a characteristic and/or value of the solution or chemical 302. In some examples, the heater 110 heats the solution to more rapidly evaporate the solution or chemical 302 and leave one or more particle(s) on the nanostructures 112 and/or the nanoparticles 114. The particle(s) may contain the analyte being tested for. In some examples, the evaporation of the solution or chemical 302 pulls and/or causes the nanostructures 108 to be positioned closer together.

Figure 4:
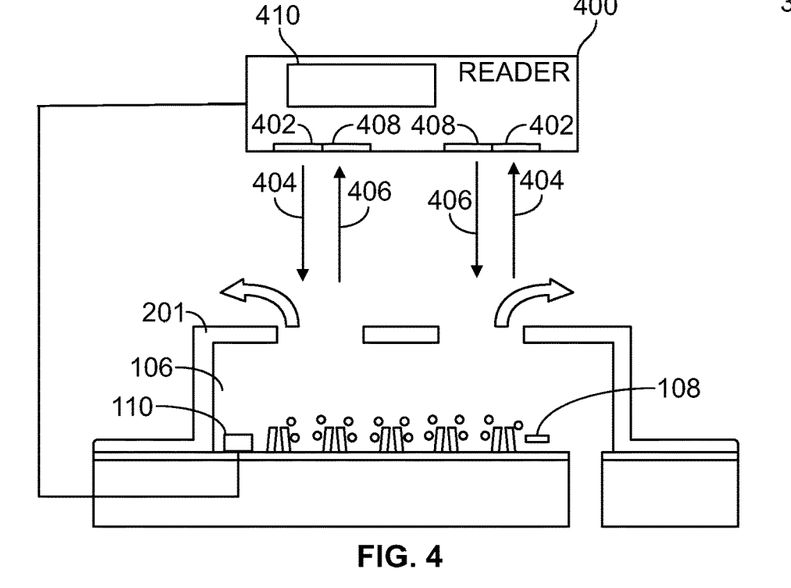
FIG. 4 depicts the example testing device of FIG. 2 and an example reading device constructed in accordance with the teachings of this disclosure.

FIG. 4 illustrates the example testing device 200 of FIG. 2 after exposure to an environment that may or may not contain an analyte(s) and/or after the solution or chemical 302 has been added to the chamber 106. FIG. 4 also illustrates an example reading device 400 constructed in accordance with the teachings of this disclosure. In this example, the reading device 400 includes a light source 402 that emits photons 404 into the chamber 106. In the illustrated example, the photons are scattered by the nanostructures 112 and/or nanoparticles 114. In some examples, some of the scattered photons 406 are detected and/or monitored by a spectrometer and/or photodetector 408 of the reading device 400. Whether the substance in question has been detected depends on one or more characteristics of the scattered photos 606 (e.g., a frequency shift, a wavelength change, etc.). In some examples, the reading device 400 uses the detected and/or monitored photons 406 along with appropriate guiding and/or filtering components to generate results (e.g., information relating to the presence or absence of an analyte to be detected) which are displayed on a monitor 410. Additionally or alternatively, in some examples, the reading device 400 receives the measured value(s) from the sensor 110 and compares the measured value(s) to reference values to determine a characteristic of the substance or chemical. The characteristic, which may be displayed on the monitor 410, may be the name of an analyte contained within the substance or chemical.

Figure 5:
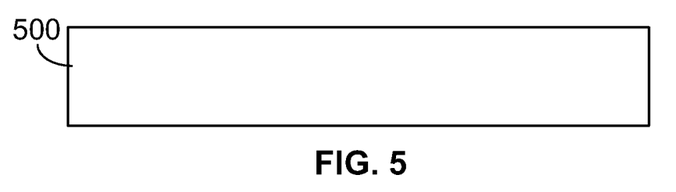
FIGS. 5-12 depict an example process of producing an example orifice plate that can be used to implement the example testing device of FIGS. 1 and/or 2.
Figure 6:
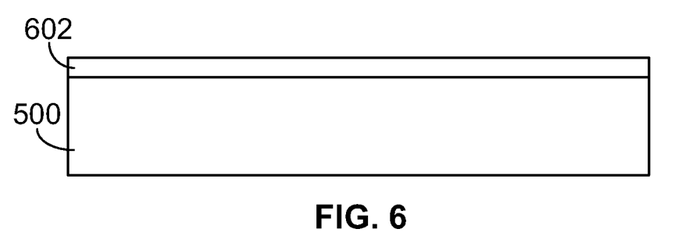
Figure 7:
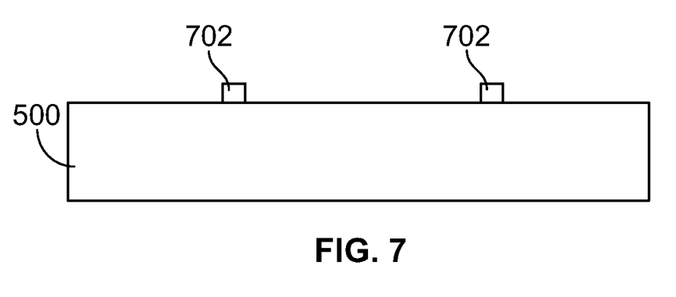

FIGS. 5-12 depict an example process of producing a portion of an example orifice plate 1200 that can be used to implement the example orifice plate(s) 104 and/or 201 of FIGS. 1 and/or 2. In the illustrated example and as shown in FIGS. 5-7, the orifice plate 1200 is produced using a mandrel 500. The photoresist 602 (FIG. 6) is applied to the mandrel 500 and patterned to form photoresist structure(s) 702 (FIG. 7). The photoresist structure(s) 702 serve as mask(s) during a subsequent etching process. The mandrel 502 may be made of glass, soda-lime-silica glass, etc.

Figure 8:
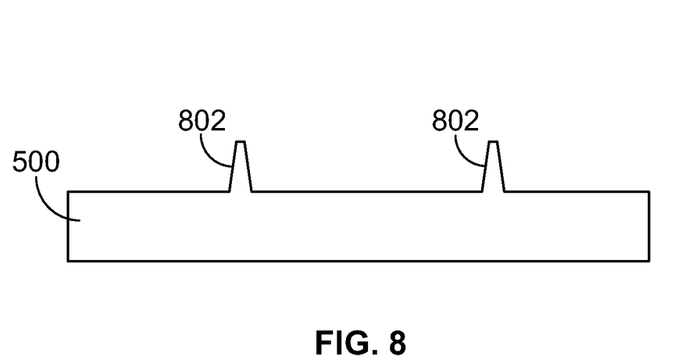

FIG. 8 shows the mandrel 500 after it has undergone wet etching using hydrogen fluoride. The photoresist structure 702 functions as mask during the wet etching and, thus, the area(s) directly under the mask are not etched. After the photoresist structure(s) 702 are removed, elongated, trapezoidal and/or conical structure(s) 802 remain, at locations which were previously beneath the photoresist mask.

Figure 9:
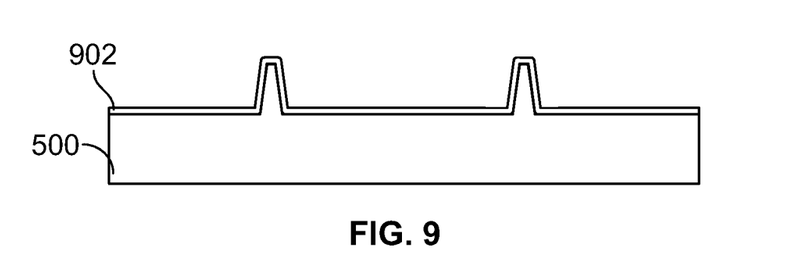

FIG. 9 depicts the example mandrel 500 after undergoing a physical vapor deposition process to add (e.g., sputter on) a layer 902 of stainless steel and/or chrome that forms a mandrel mask on the mandrel 500.

Figure 10:
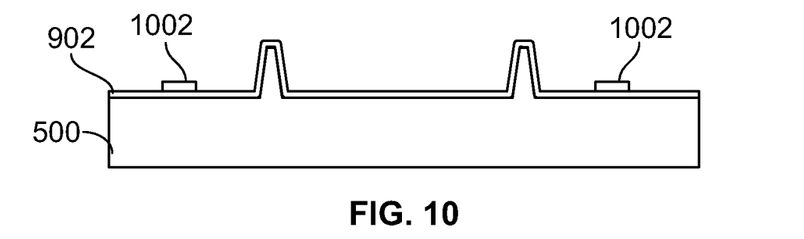

FIG. 10 depicts the example mandrel 500 after undergoing plasma-enhanced chemical vapor deposition (PECVD) and photolithography processes. The PECVD process deposits silicon carbide on the layer 902 and the photolithography process patterns the deposited silicon carbide to form silicon carbide structure(s) 1002 used to define corresponding aperture(s) 1202 of the orifice plate 1200.

Figure 11:
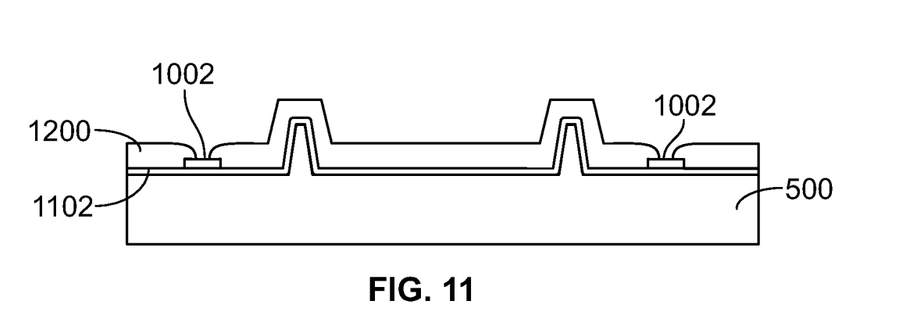
Figure 12:
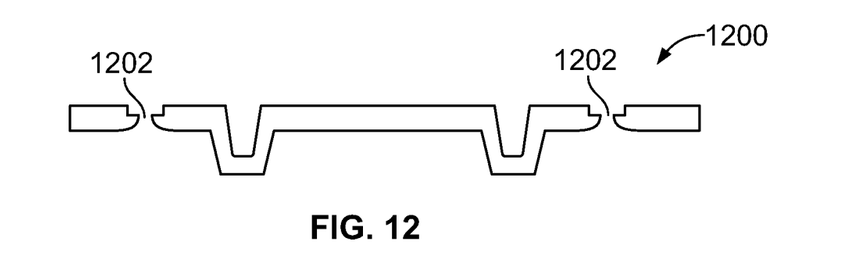

To form the orifice plate 1200, in some examples and as shown in FIG. 11, the mandrel 500 is immersed in a nickel plating bath that plates a surface 1102 of the mandrel 500 everywhere except where the nonconductive silicon carbide 1002 is located. The nickel from the bath, thus, defines the pattern(s), shape(s) and/or feature(s) of the orifice plate 1200. After the mandrel 500 and the orifice plate 1200 are removed from the plating bath, the orifice plate 1200 may be removed and/or peeled off of the mandrel 500 as illustrated in FIG. 12. In the example of FIG. 12, aperture(s) are located at position(s) corresponding to the silicon carbide structure(s) 1002 of FIGS. 10 and 11.

Figure 13:
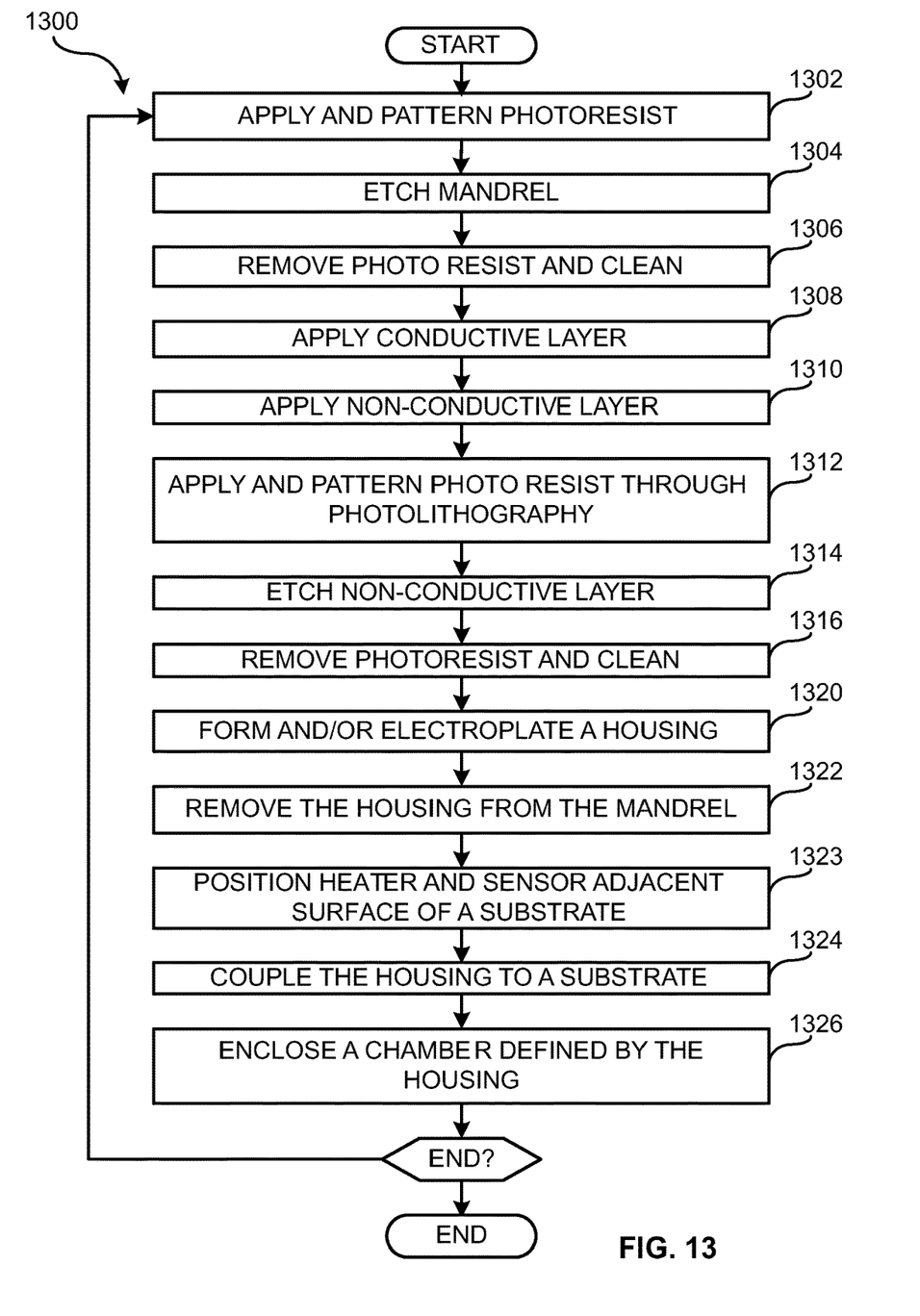
FIG. 13 illustrates an example method of making the example testing devices of FIGS. 1-4.

FIG. 13 illustrates an example method 1300 of manufacturing the example testing devices of FIGS. 1-12. Although the example method 1300 of FIGS. 1-12 are described with reference to the flow diagram of FIG. 13, other methods of implementing the method 1300 may be employed. For example, the order of execution of the blocks may be changed, and/or some of the blocks described may be changed, eliminated, sub-divided and/or combined.

The example method 1300 of FIG. 13 begins by applying and patterning photoresist on the mandrel 500 through photolithography (block 1302). In some examples, the mandrel 500 is etched (e.g., wet etched, reactive-ion etched (RIE)) using hydrogen fluoride after which the photoresist structure 702 is removed and the mandrel 500 is cleaned to show elongated, trapezoidal and/or conical structure(s) 802, which were previously beneath the photoresist mask (blocks 1304, 1306). To form a mandrel mask on the mandrel 500, the mandrel 500 may undergo a physical vapor deposition process to add (e.g., sputter on) the layer 902 of conductive material, stainless steel and/or chrome (block 1308). To apply the non-conductive layer and/or silicon carbide to define the corresponding aperture(s) 1202 of the orifice plate 1200, the mandrel 500 may undergo plasma-enhanced chemical vapor deposition (PECVD) and photolithography processes (block 1310). Photoresist may be applied and patterned on the mandrel 500 through photolithography (block 1312). In some examples, the non-conductive layer is etched (e.g., wet etched, reactive-ion etched (RIE)) using hydrogen fluoride after which the photoresist structure 702 is removed and the mandrel 500 is cleaned (blocks 1314, 1316).

To form the orifice plate 1200, in some examples, the mandrel 500 is positioned and/or immersed in a plating bath to form a metal housing and/or orifice plate 104, 201 and/or electroplated with, for example, gold, palladium and/or rhodium (block 1320). In some examples, the conductiveness of the housing 104, 201 enables the housing 104, 201 to act as an electronic terminal for sampling. The plating bath may include a metal such as nickel, gold and/or platinum. In some examples, the metal of the plating bath does not plate against the silicon carbide because the silicon carbide is nonconductive. Thus, apertures 130 of the housing 104, 201 are defined where the silicon carbide is located and the silicon carbide may, thus, be used to control the size of the apertures 130.

After a particular amount of time, in some examples, the mandrel 500 and the housing 104, 201, 1302 are removed from the plating bath and the housing 104, 201 is removed and/or peeled from the mandrel 500 (block 1322). A sensor 108 and a heater 110 is positioned adjacent the surface 115 of the substrate 102 (block 1323). The housing 104, 201 of the illustrated example is then coupled to the substrate 102 such that the sensor 108, the heater 110 and the nanoparticles 114 are positioned within a chamber 106 defined by the housing 104, 201 (blocks 1324). To enclose the chamber 106 and/or cover apertures 130 defined by the housing 104, 201, a seal 132 is coupled to the housing 104, 201, 1302 (block 1326). The method 1300 then terminates or returns to block 1302.

Figure 14:
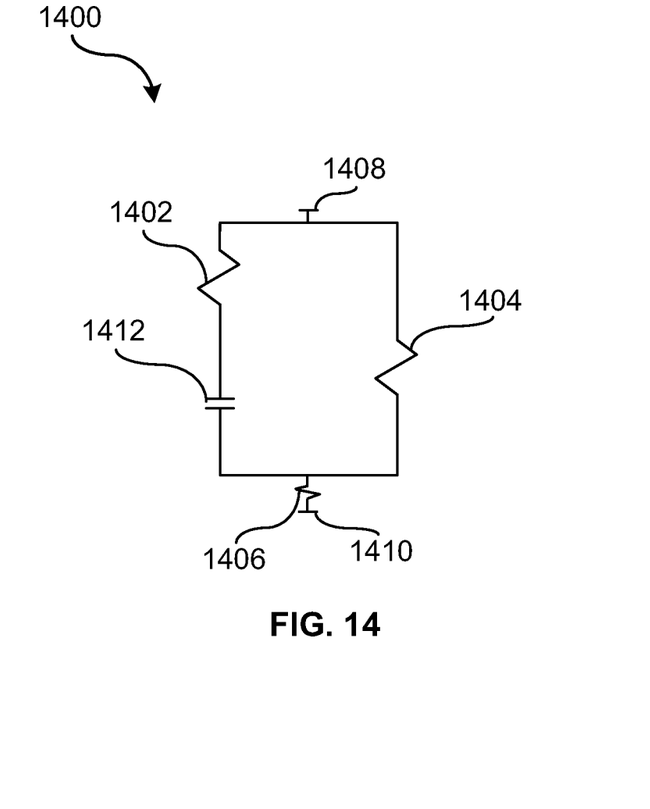
FIG. 14 depicts an example model that can be used to represent the examples disclosed herein.

FIG. 14 depicts an example substance, ink and/or chemical model 1400 that can be used in an analysis circuit in accordance with the teachings of this disclosure. The model 1400 includes a first resistor 1402, a second resistor 1404, a third resistor 1406, electrodes 1408, 1410 and a capacitor 1412. In some examples, a capacitance of the capacitor 1412 corresponds to the capacitance of an electric double-layer capacitor of the substance and/or chemical in the chamber 106. In some examples, the first resistor 1402 corresponds to the resistance of a bulk body of the substance and/or chemical in the chamber 106. In some examples, a resistance of the first resistor 1402 is determined by ion concentration and/or magnitude and is proportional to the chemical path length and/or cross-sectional area. In some examples, the resistance of the second resistor 1404 corresponds to the leakage path resistance of the bulk body of the substance and/or chemical in the chamber 106 and/or the path having a direct conducting path. In some examples, the third resistor 1410 corresponds to the parasitic resistance in the sensor circuit, which may be associated with the metal layer conducting paths, contacts, etc.

Based on the model 1400, in some examples, a transfer function is developed for the gain (Vout/Vin). In some examples, the different resistances and/or properties of the substance and/or chemical in the chamber 106 provide a frequency response and/or signal. In some examples, the frequency response can be analyzed to identify parameters and/or characteristics of the substance and/or chemical in the chamber 106.

As set forth herein, an example device to detect a substance includes a housing defining a first chamber. A substrate is coupled to the housing. The substrate includes nanostructures positioned within the first chamber. The nanostructures are to react to the substance when exposed thereto. The device includes a first heater positioned within the first chamber. The heater is to heat at least a portion of the substance to ready the device for analysis. In some examples, the first heater includes a resistor. In some examples, the device includes a sensor positioned within the first chamber. The sensor is to measure a parameter value of the substance. The sensor is different than the nanostructures. In some examples, the sensor includes a capacitor. In some examples, the parameter value includes at least one of impedance or capacitance.

In some examples, the device includes a seal to enclose at least a portion of the first chamber to protect the nanostructures from premature exposure. In some examples, the seal includes at least one of a transparent material, a flexible material, a removable material, or a polymer material. In some examples, the housing includes nickel, gold, platinum, palladium, or rhodium. In some examples, the housing includes an orifice plate. In some examples, the housing is electroplated with at least one of gold, palladium, or rhodium. In some examples, the substrate includes at least one of a Surface Enhanced Raman spectroscopy substrate, a self actuating Surface Enhanced Raman spectroscopy substrate, an Enhanced Fluorescence spectroscopy substrate, or an Enhanced Luminescence spectroscopy substrate. In some examples, the housing defines a second externally accessible chamber. The nanostructures are additionally positioned within the second chamber. In some examples, the device includes a second heater positioned within the second chamber. The second heater is to heat at least a portion of the substance to shorten a time until the second chamber is ready for analysis.

An example device to detect a substance includes a housing defining a chamber. A substrate is coupled to the housing. The substrate includes nanostructures positioned within the chamber. The nanostructures are to react to the substance when exposed thereto. The device includes a sensor positioned within the chamber. The sensor is to measure a parameter value of the substance. The sensor is different than the nanostructure.

An example method of producing a device to detect a substance includes immersing a mandrel in a plating bath to form a housing. The mandrel includes a pattern or a structure corresponding to a desired aperture or a structure of the housing. The method includes removing the housing from the mandrel and coupling the housing to a substrate. The housing is to define a chamber in which a heater and nanostructures of the substrate are positioned. The nanostructures are to evidence exposure to the substance if exposed thereto.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A device to detect a substance, comprising:
   a housing defining a first chamber;
   a substrate coupled to the housing, the substrate comprising nanostructures positioned within the first chamber, the nanostructures to react to the substance when exposed thereto, wherein the nanostructures comprise pillars having ends that close together in response to evaporation of the substance; and
   a first heater positioned within the first chamber, the heater to heat at least a portion of the substance to evaporate the substance to ready the device for analysis.

2. The device of claim 1, wherein the first heater comprises a resistor.

3. The device of claim 1, further comprising a sensor positioned within the first chamber, the sensor to measure a parameter value of the substance, the sensor different than the nanostructures.

4. The device of claim 3, wherein the sensor comprises a capacitor.

5. The device of claim 3, wherein the parameter value comprises at least one of impedance or capacitance.

6. The device of claim 1, further comprising a seal to enclose at least a portion of the first chamber to protect the nanostructures from premature exposure.

7. The device of claim 6, wherein the seal comprises at least one of a transparent material, a flexible material, a removable material, or a polymer material.

8. The device of claim 1, wherein the housing comprises nickel, gold, platinum, palladium, or rhodium.

9. The device of claim 1, wherein the housing comprises an orifice plate extending opposite the substrate over the nanostructures with the nanostructures extending between the substrate and the orifice plate, the orifice plate having an orifice facing the substrate.

10. The device of claim 1, wherein the substrate comprises at least one of a Surface Enhanced Raman spectroscopy substrate, a self actuating Surface Enhanced Raman spectroscopy substrate, an Enhanced Fluorescence spectroscopy substrate, or an Enhanced Luminescence spectroscopy substrate.

11. The device of claim 1, wherein the housing comprises a single orifice plate extending opposite the substrate, the single orifice plate having a first portion extending over the nanostructures to define the first chamber having a first interior with the nanostructures being sandwiched between the substrate and the first portion, the single orifice plate further having a second portion extending over second nanostructures to define a second chamber having a second interior with the nanostructures being sandwiched between the substrate and second portion, the first interior being distinct and disconnected from the second interior, the second nanostructures to react to the substance and should comprising pillars, the pillars of the second nanostructures having ends that close together in response to evaporation of the substance.

12. The device of claim 11, further comprising a second heater positioned within the second chamber, the second heater to heat at least a portion of the substance to shorten a time until the second chamber is ready for analysis.

13. The device of claim 1 further comprising a bore through the housing opposite the substrate and opposite the nanostructures.

14. The device of claim 13 further comprising an inlet opening through the substrate.

15. The device of claim 1, wherein the first heater is to heat at least the portion of the substrate from the substrate to evaporate the substance to ready the device for analysis.

16. A device to detect a substance, comprising:
a housing defining a chamber;
a substrate coupled to the housing, the substrate comprising nanostructures positioned within the chamber, the nanostructures to react to the substance when exposed thereto;
a sensor positioned within the chamber, the sensor to measure a parameter value of the substance, the sensor different than the nanostructures; and
a bore through the housing opposite the substrate and opposite the nanostructures.

17. The device of claim 16 further comprising a removable seal covering the bore.

18. The device of claim 16 wherein the nanostructures comprise pillars having ends that-close together in response to evaporation of the substance.

19. The device of claim 16, wherein the housing comprises an orifice plate over an interior of the chamber containing the nanostructures, the orifice plate comprising a plurality of bores through the orifice plate opposite the interior, opposite the substrate and opposite the nanostructures, the plurality of bores providing the bore through the housing.

20. The device of claim 19, further comprising:
a heater within the interior of the chamber; and
a seal covering each of the plurality of bores.

* * * * *